United States Patent [19]

Cavazza

[11] Patent Number: 5,869,528
[45] Date of Patent: Feb. 9, 1999

[54] THERAPEUTICAL METHOD FOR THE TREATMENT OF ATTENTION-DEFICIT/ HYPERACTIVE DISORDERS

[75] Inventor: Claudio Cavazza, Rome, Italy

[73] Assignee: Sigma-Tau Industrie Farmaceutiche Riunite S.p.A., Rome, Italy

[21] Appl. No.: 898,433

[22] Filed: Jul. 22, 1997

[51] Int. Cl.[6] .................................................. A61K 31/205
[52] U.S. Cl. ............................................. 514/556; 514/23
[58] Field of Search ....................................... 514/556, 23

[56] References Cited

U.S. PATENT DOCUMENTS 4,346,107  8/1982  Cavazza et al. ........................ 424/316

OTHER PUBLICATIONS

Chemical Abstracts vol. 107: 198928c (Chemiosyntex), 1987.

Chemical Abstracts vol. 108: 216210q (Nappi et. al.), 1988.

*Primary Examiner*—Leonard Schenkman
*Attorney, Agent, or Firm*—Oblon, Spivak, McClelland, Maier & Neustadt, P.C.

[57] ABSTRACT

A therapeutical method for the treatment of Attention-Deficit/Hyperactive Disorder (ADHD) is disclosed which comprises administering to a child in need thereof L-carnitine or an alkanoyl L-carnitine or a pharmacologically acceptable salt thereof.

6 Claims, No Drawings

THERAPEUTICAL METHOD FOR THE TREATMENT OF ATTENTION-DEFICIT/HYPERACTIVE DISORDERS

BACKGROUND OF THE INVENTION

1. Field of the Invention

The present invention relates to a therapeutical method for treating children affected by learning disorders and, more specifically, to a method for treating children suffering from Attention-Deficit/Hyperactive Disorder (ADHD).

2. Description of the Prior Art

ADHD is a developmentally inappropriate inattention and impulsivity generally associated with hyperactivity.

ADHD diagnostic criteria are precisely set forth in the Diagnostic and Statistical Manual of Mental Disorders, Fourth Edition (DSM-IV), pages 82–85, published by the American Psychiatric Association.

ADHD diagnosis should in fact be made with great care and only if the symptoms of inattention or hyperactivity are excessive for the child's mental age. Inattention in the classroom may also occur when children with high intelligence are placed in academically understimulating environments.

ADHD is a heterogenous disorder of unknown etiology. It is one of the major clinical and public health problems worldwide because of its associated morbidity and disability in children and adolescents.

Its impact on society is enormous in terms of the financial cost, the stress to families, the impact on academic and vocational activities. The symptoms of this syndrome are distressing to the environment (parents and teachers) and also distressful to the child. The disorder is usually accompanied by impairment of social and school functioning and in the majority of cases persists throughout childhood.

Moreover, prospective longitudinal studies of hyperkinetic children indicate that a substantial proportion thereof retains hyperkinetic symptoms and goes on to antisocial disorders.

ADHD affects approximately 5 to 10% of school-aged children youths according to epidemiological studies carried out in the United States and Europe. ADHD is seen 10 times more frequently in boys than in girls.

ADHD is a common cause of referrals to pediatricians and child psychiatrists and accounts approximately for as 50% of child psychiatric clinic population.

The affected children do not necessarily share a common set of characteristics. However, most of the children show deficiencies in their attention span, impulse control, and rule-governed behaviour. The common hyperactivity and impulsivity symptoms are described as follows. The children often fidget with hands or feet, leave seat in the classroom or at home during meals, have difficulty awaiting turn, blurt out answers before questions have been completed, often talk excessively, interrupt or intrude on others, often run about in situations in which it is inappropriate.

On the other side the common inattention symptoms are described as follows. The children often fail to give attention to details or make careless mistakes in school work or other daily activities. They also have difficulty in sustaining attention in tasks or play activities, are easily distracted by extraneous stimuli, often do not seem to listen when spoken to directly, do not follow through on instructions and fail to finish school work or daily duties. Often they are unmotivated to do school or home work, avoid tasks that require sustained mental effort, often lose things necessary for tasks or activities and are forgetful in common daily activities. In some children the hyperactivity-impulsivity are predominant on the attention deficit disorder, whereas in other children the attention deficit is predominant. Mostly the hyperactivity-impulsivity and attention deficit symptoms are combined.

As previously indicated, ADHD etiology is unknown. Genetic factors, prenatal and perinatal acquired brain damage have been proposed as causes of the disease; yet no definitive conclusions has been reached. Recently, it has been suggested that the affected children are suffering from a disorder in energetical regulation mechanisms.

The psychopharmacological agents so far proposed to treat the disease are stimulant compounds (amphetamine and methylfenidate), tricyclics antidepressants (imipramine, amitryptiline) and antipsychotic agents (phenothiazines, haloperidol).

Two compounds are mostly used worldwide: methylfenidate and clonidine. The latter is primarily used as a central antihypertensive agent.

Methylfenidate has been object of several clinical studies that have proved a good efficacy both in hyperactivity and in attention deficit. However, rebound of hyperactivity has been often reported and sometimes impulsivity has been shown to increase.

Frequent adverse effects are reported during treatment with methylfenidate such as weary dark rings under the eyes, enlarged pupils, headache and decreased appetite.

Also difficulty in falling asleep, night awakening, bed wetting, drowsiness, reduction of systolic and diasystolic blood pressure have been reported. The most common side effects are insomnia, decreased appetite and weight loss.

Clonidine is also effective on home/school hyperactivity and on attention disorders but its beneficial effects on target problems with teachers and parents are less significant than those achieved with methylfenidate.

The adverse effects of clonidine are various and frequent. Drowsiness is the most common. An increased need for short naps has been also reported.

Frequent are also night awakening, sometimes accompanied by nightmares. Also nausea, decreased appetite and dry mouth have been reported. Reduction of systolic and diasystolic blood pressure occurs more frequently than with methylfenidate treatment.

The adverse effects of both compounds, i.e., methylfenidate and clonidine, have been recorded during the clinical trials and also reported by patients not participating to the trials as well as by parents and teachers.

It is, therefore, an object of the present invention to provide a therapeutical method for the treatment of children suffering from ADHD which comprises administering to children in need thereof a drug which is not only at least as effective as the known drugs, but which also does not present the aforesaid drawbacks and objectionable side effects of the known drugs.

SUMMARY OF THE INVENTION

This object is achieved by the present invention which provides a method for the treatment of Attention-Deficit/Hyperactive Disorders (ADHD) which comprises orally or parenterally administering to a child in need thereof in a single or multiple dose administration regimen a therapeutically effective amount of L-carnitine or alkanoyl L-carnitine wherein the alkanoyl group, straight or branched, has 2–8, preferably 2–5, carbon atoms or a pharmacologically acceptable salt thereof.

DESCRIPTION OF THE SPECIFIC EMBODIMENTS

Preferred alkanoyl L-carnitines are acetyl, propionyl, butyryl, valeryl and isovaleryl L-carnitine. Acetyl L-carnitine, propionyl L-carnitine and isovaleryl L-carnitine are particularly preferred.

In actual practice L-carnitine, the alkanoyl L-carnitine or the pharmacologically acceptable salt thereof are administered parenterally or orally in any of the usual pharmaceutical forms. These include solid and liquid oral unit dosage forms such as tablets, capsules, powders, solutions, syrups and the like, including sustained release preparations, and fluid injectable forms such as sterile solutions and suspensions. The term unit dosage form as used in this specification refer to physically discrete units to be administered in single or multiple dosage, each unit containing in association with the carrier, the predetermined quantity of L-carnitine, or a molar equivalent amount of an alkanoyl L-carnitine or a pharmaceutically acceptable salt thereof, calculated to produce the desired effect upon administration of a specific number, one or more, of such units.

The dose of L-carnitine, alkanoyl L-carnitine or pharmacologically acceptable salt thereof which is administered should be determined having regard to the age, weight and condition of the child, using sound professional judgment. Although effective results can be noticed at doses of L-carnitine as low as from 30 to 40 mg/kg of body weight daily, a dose of from about 50 to about 120 mg/kg of body weight daily is preferred. Alternatively, molar equivalent amounts of alkanoyl L-carnitine or pharmacologically acceptable salts of both L-carnitine and alkanoyl L-carnitine can be effectively used as well.

Should it be deemed necessary, larger doses can be safely administered because of the extremely low toxicity of L-carnitine, the alkanoyl L-carnitines and their salts. In view of the nature of the desired biochemical response, it is often desirable to divide the daily dosage into several administrations, utilizing a multidose regimen, the response being gauged in view of the total amount administered.

Typical examples of L-carnitine containing compositions for oral and parenteral administration are as follows:

EXAMPLE 1

Solution or sterile aqueous solutions in concentrations from 50 mg to 500 mg per ml.
A. An injectable composition (for ampoules/vials) is prepared as follows
   L-carnitine: 50 ml
   Water for injections: q.s. 1 ml
B. An intravenous composition is prepared in accordance with the following
   L-carnitine: 50 g
   NaCl: 8.6 g
   KCl: 0.3 g
   CaCl$_2$: 0.33 g
   Water for injections: q.s. 1 liter
C. A composition for oral use is prepared in accordance with the following non-limitative composition:
   L-carnitine: 5 g
   Mannitol: 1.1 g
   Sorbitol: 60 g
   Methyl p-oxybenzoate: 0.100 g
   Propyl p-benzoate: 0.050 g
   Orange extract: 20 g
   Vitamine B$_{12}$: 300 mcg
   Purified water: q.s. 10 ml

EXAMPLE 2

Tablets containing from 200 mg to 400 mg of L-carnitine are prepared in accordance with the following:
   L-carnitine: 200 g
   Starch: 100 g
   Avicel: 150 g
   Talc: 50 g The ingredients are thoroughly mixed and compressed into tablets of 1 g weight.

EXAMPLE 3

Capsules containing 500 mg of L-carnitine can be prepared without excipients or by admixture with an inert carrier and by introduction into a gelatine sheath.

The preparations of similar compositions wherein any of the aforesaid alkanoyl L-carnitines substitutes for L-carnitine shall be readily apparent to any average-skilled pharmaceutical technologist.

Pharmaceutically acceptable salts of L-carnitine or the aforesaid alkanoyl L-carnitines include, in addition to their inner salts, all pharmaceutically acceptable salts which are prepared by addition of an acid to L-carnitine or the alkanoyl L-carnitine and which do not give rise to undesired toxic or side effects. The formation of pharmaceutically acceptable acid addition salts is well known in pharmaceutical technology.

Non-limiting examples of suitable salts include the chloride, bromide, orotate, aspartate, acid aspartate, acid tartrate, acid citrate, acid phosphate, fumarate, acid fumarate, lactate, maleate, acid maleate, acid oxalate, acid sulphate, glucose phosphate, tartrate and acid tartrate salts. Other suitably acceptable salts which are non-toxic and provide substantially similar results to administration of L-carnitine, alkanoyl L-carnitines and the above-identified pharmaceutical salts will be readily apparent to one having ordinary skill in the art and are considered to be equivalent to the salts enumerated above.

A clinical study showing the efficacy of L-carnitine in the therapeutical treatment of ADHD is hereinbelow described.

A group of children affected by Attention-Deficit/Hyperactive Disorders (ADHD) under treatment with standard therapy (stimulant drugs) who complained to suffer from fatigue was submitted to an additional treatment with L-carnitine that is widely used to cure or improve this specific symptom. L-carnitine treatment not only improved the symptom of fatigue, but, unexpectedly, brought about a major improvement in their ADHD behaviour. After cessation of the L-carnitine medication, the ADHD symptoms returned. The reintroduction of L-carnitine treatment caused a marked improvement in the ADHD symptoms.

This observation prompted the carrying out of a clinical study aimed at properly investigating the activity of L-carnitine on ADHD target symptoms.

25 children diagnosed with ADHD were enrolled in the study.

The diagnostic selection criteria according to DSM-IV were established by paediatric psychiatrists or paediatric psychologists in a center specialized for the treatment of ADHD.

All the patients of both sexes were living in a family home and not in an institution. Twenty were males and five females, aged four to twelve years.

Eight patients out of 25 were prevailingly affected by Attention Deficit symptoms, seven prevailingly by Hyperactivity/impulsivity symptoms and ten by the two combined disorders.

The selected children did not benefit from stimulant medications or had developed persistent undesired adverse events during the treatment with stimulants such as difficulty in falling asleep or nightly awakening and decreased appetite. All standard treatments were stopped and replaced by L-carnitine, at the dose of 100 mg/kg per day in the form of an oral solution. The treatment lasted twelve weeks. Clinical evaluation was performed at basal time (two observations) and at weeks four, eight and twelve.

The clinical evaluation was done by means of Groningen's Parent Observation Scale [see Boorsma S. (1990), The parent version of the Groningen Behaviour Observation scale: Factor structure and norms. In A. F. Kalverboer (Ed.), Developmental Biopsychology: Experimental and observational studies in children at risk (pp. 293–298). Ann. Arbor: University of Michigan Press] and two Teacher Observation Scales, namely Groningen's scale [see Vaessen W. (1990), The teacher version of the Groningen Behaviour Observation scale: Factor structure and norms. In A. F. Kavelboer (Ed.), Developmental Biopsychology: Experimental and observational studies in children at risk (pp. 287–291). Ann. Arbor.: University of Michigan Press] and Conner's scale [see Werry J. S., Sprague R. L., & Cohen M. N. (1975), Conners' Teacher Rating Scale for use in drug studies with children: An empirical study. Journal of Abnormal Child Psychology 3, 217–229].

The Groningen Behaviour Observation Scale, parent version, groups 15 target symptoms of ADHD and was designated taking into account the peculiar perceptiveness of the parents and the daily tasks of the home life. Both Attention and Hyperactivity symptoms are included.

The Groningen Behaviour Observation Scale, teacher version, also groups 15 target symptoms and was designated taking into account the peculiar tasks of school working as well as the perceptiveness of a teacher.

Conner's Teacher Rating Scale is composed by 39 descriptive terms of behaviour. It is commonly used and validated worldwide, to study the activity of the compounds proposed for the therapy of the ADHD.

The response to the L-carnitine treatment was evaluated as a global clinical impression coming out from the three rating scales.

The response was rated positive only when the target symptoms disappeared or decreased markedly. The scores for symptoms were as follows: 1=not at all; 2=just a little; 3=pretty much; 4=very much. The response was defined positive for scores 1 and 2.

Based on these criteria for evaluation of the test compound activity, at week twelve (end of treatment) the response to L-carnitine was considered positive in six children prevailingly affected by Attention Disorders, six children prevailingly affected by Hyperactivity/Impulsivity Disorders, and eight children affected by the combined symptoms. The positive response accounts for a total of twenty patients out of twenty-five, i.e. 80% of the treated population.

The patients were also evaluated for safety during the screening and at week twelve.

Neither adverse drug side effects defined as noxious or pathologic, nor changes in anatomical, physiological or metabolic functions were reported. A minor side effect whether or not related to the treatment was reported, i.e. two patients complained about an unfamiliar odor of the faeces.

What is claimed is:

1. A method for the treatment of Attention-Deficit/Hyperactive Disorder (ADHD), which comprises: orally or parenterally administering to a child in need thereof in a single or multiple dose administration regimen a therapeutically effective amount of L-carnitine or an alkanoyl L-carnitine, wherein the alkanoyl group, straight or branched, has 2–8 carbon atoms or a pharmacologically acceptable salt thereof.

2. The method of claim 1, wherein the total amount administered per day is from about 30 to about 120 mg of L-carnitine, or a molar equivalent amount of alkanoyl L-carnitine or a pharmacologically acceptable salt thereof, per kilogram of body weight.

3. The method of claim 2, wherein the total amount administered per day is from about 50 to about 100 mg of L-carnitine, or a molar equivalent amount of alkanoyl L-carnitine or a pharmacologically acceptable salt thereof, per kilogram of body weight.

4. The method of claim 1 wherein the alkanoyl L-carnitine has 2–5 carbon atoms.

5. The method of claim 4, wherein the alkanoyl L-carnitine is selected from the group consisting of acetyl, propionyl, butyryl, valeryl and isovaleryl L-carnitine.

6. The method of claim 1, wherein the pharmacologically acceptable salt of L-carnitine or alkanoyl L-carnitine is selected from the group consisting of chloride, bromide, orotate, aspartate, acid aspartate, acid tartrate, acid citrate, acid phosphate, fumarate, acid fumarate, lactate, maleate, acid maleate, acid oxalate, acid sulphate, glucose phosphate, and tartrate.

* * * * *